(12) United States Patent
Jeannin et al.

(10) Patent No.: US 11,278,101 B2
(45) Date of Patent: Mar. 22, 2022

(54) FLUID PRODUCT DISPENSING AND APPLICATION ASSEMBLY

(71) Applicant: APTAR FRANCE SAS, Le Neubourg (FR)

(72) Inventors: Julien Jeannin, Louviers (FR); Arnaud Leboucher, Ecardenville La Campagne (FR)

(73) Assignee: APTAR FRANCE SAS, Le Neubourg (FR)

( * ) Notice: Subject to any disclaimer, the term of this patent is extended or adjusted under 35 U.S.C. 154(b) by 270 days.

(21) Appl. No.: 16/486,598

(22) PCT Filed: Mar. 6, 2018

(86) PCT No.: PCT/FR2018/050510
§ 371 (c)(1),
(2) Date: Aug. 16, 2019

(87) PCT Pub. No.: WO2018/162837
PCT Pub. Date: Sep. 13, 2018

(65) Prior Publication Data
US 2021/0282532 A1    Sep. 16, 2021

(30) Foreign Application Priority Data

Mar. 9, 2017   (FR) ...................... 1751930

(51) Int. Cl.
*A45D 34/04*   (2006.01)
*A61N 1/32*    (2006.01)
(Continued)

(52) U.S. Cl.
CPC ............. *A45D 34/04* (2013.01); *A61N 1/325* (2013.01); *A61N 5/062* (2013.01);
(Continued)

(58) Field of Classification Search
CPC .............. A45D 34/04; A45D 2034/005; A45D 2200/56
See application file for complete search history.

(56) References Cited

U.S. PATENT DOCUMENTS 6,883,995 B1 *   4/2005   Gueret ................... A45D 34/04
                                              401/183
7,374,361 B1 *   5/2008   Kwon .................... A45D 34/04
                                              401/202
(Continued)

FOREIGN PATENT DOCUMENTS

| EP | 1 273 245 A1 | 1/2003 |
| EP | 1 535 532 A1 | 6/2005 |
| WO | 2015/170048 A1 | 11/2015 |

OTHER PUBLICATIONS

International Search Report for PCT/FR2018/050510 dated Jul. 2, 2018 [PCT/ISA/210].
(Continued)

*Primary Examiner* — J C Jacyna
(74) *Attorney, Agent, or Firm* — Sughrue Mion, PLLC

(57) ABSTRACT

A fluid dispenser and applicator assembly comprising:
a hollow reception body (1') including a housing (22'); and
a fluid dispenser (D') including angular orientation means (16, 64) for bringing the fluid dispenser (D') into a determined angular position relative to the reception body (1');
the assembly being characterized in that the angular orientation means (16, 64) cause the dispenser (D') to turn as it is pushed into the reception body (1'), until it reaches its determined angular position.

12 Claims, 3 Drawing Sheets

(51) Int. Cl.
   *A61N 5/06*     (2006.01)
   *A45D 34/00*    (2006.01)

(52) U.S. Cl.
   CPC .. *A45D 2034/005* (2013.01); *A45D 2200/056* (2013.01); *A45D 2200/205* (2013.01); *A45D 2200/207* (2013.01)

(56) References Cited

U.S. PATENT DOCUMENTS

| | | | |
|---|---|---|---|
| 2005/0042020 A1 | 2/2005 | Saito et al. | |
| 2007/0274764 A1* | 11/2007 | Shim | B43K 8/03 401/108 |
| 2009/0154984 A1* | 6/2009 | Tani | A45D 40/04 401/75 |
| 2016/0135567 A1 | 5/2016 | Kamboj | |
| 2017/0055672 A1* | 3/2017 | Duquet | A45D 34/00 |
| 2017/0247170 A1* | 8/2017 | Bilton | G01F 11/021 |

OTHER PUBLICATIONS

International Preliminary Report on Patentability issued from the International Bureau in counterpart International Application No. PCT/FR2018/050510, dated Sep. 12, 2019.

\* cited by examiner

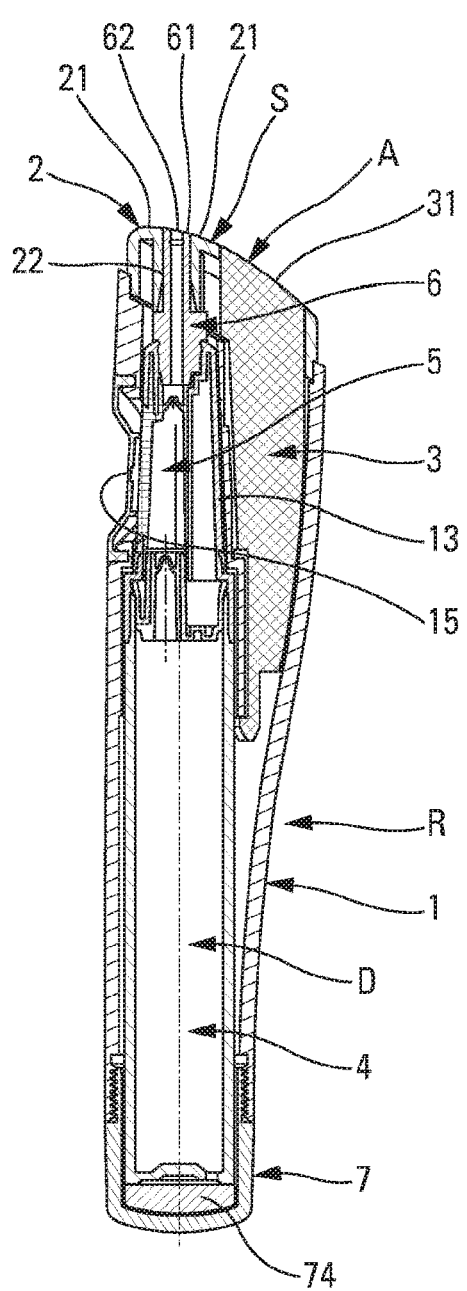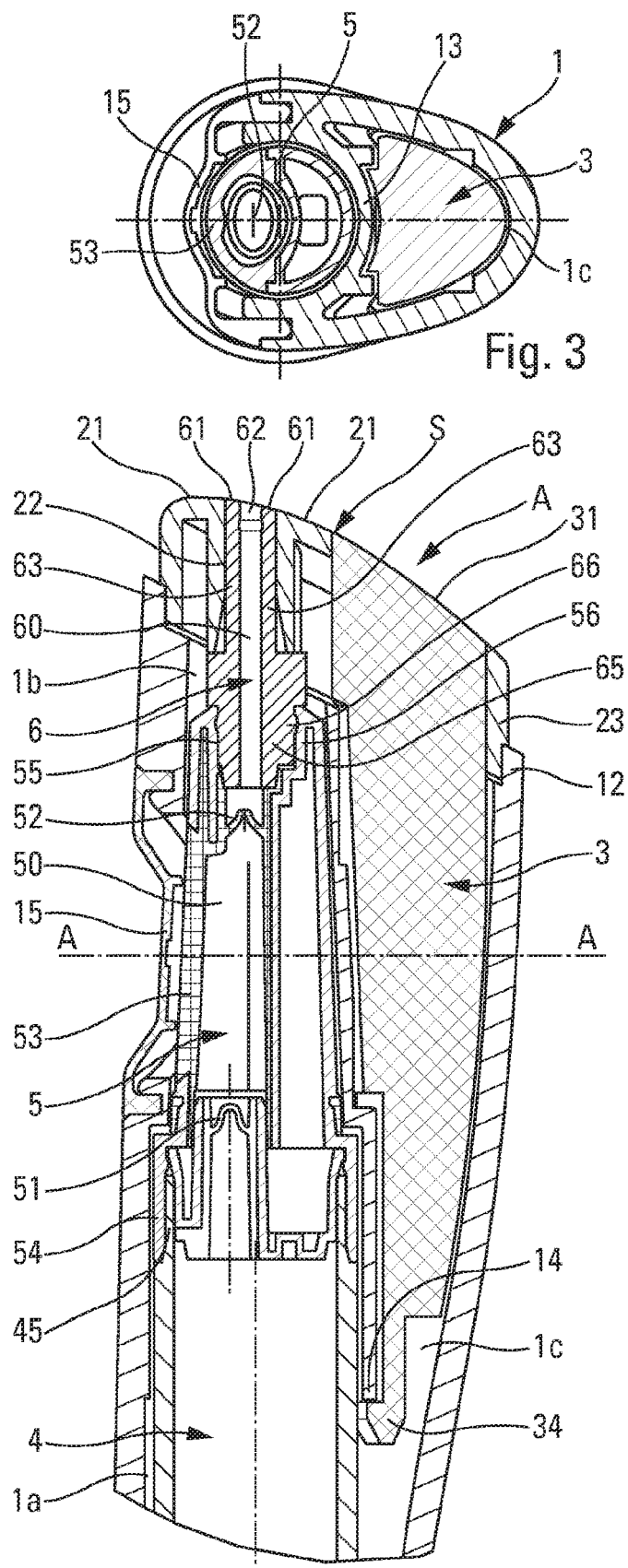

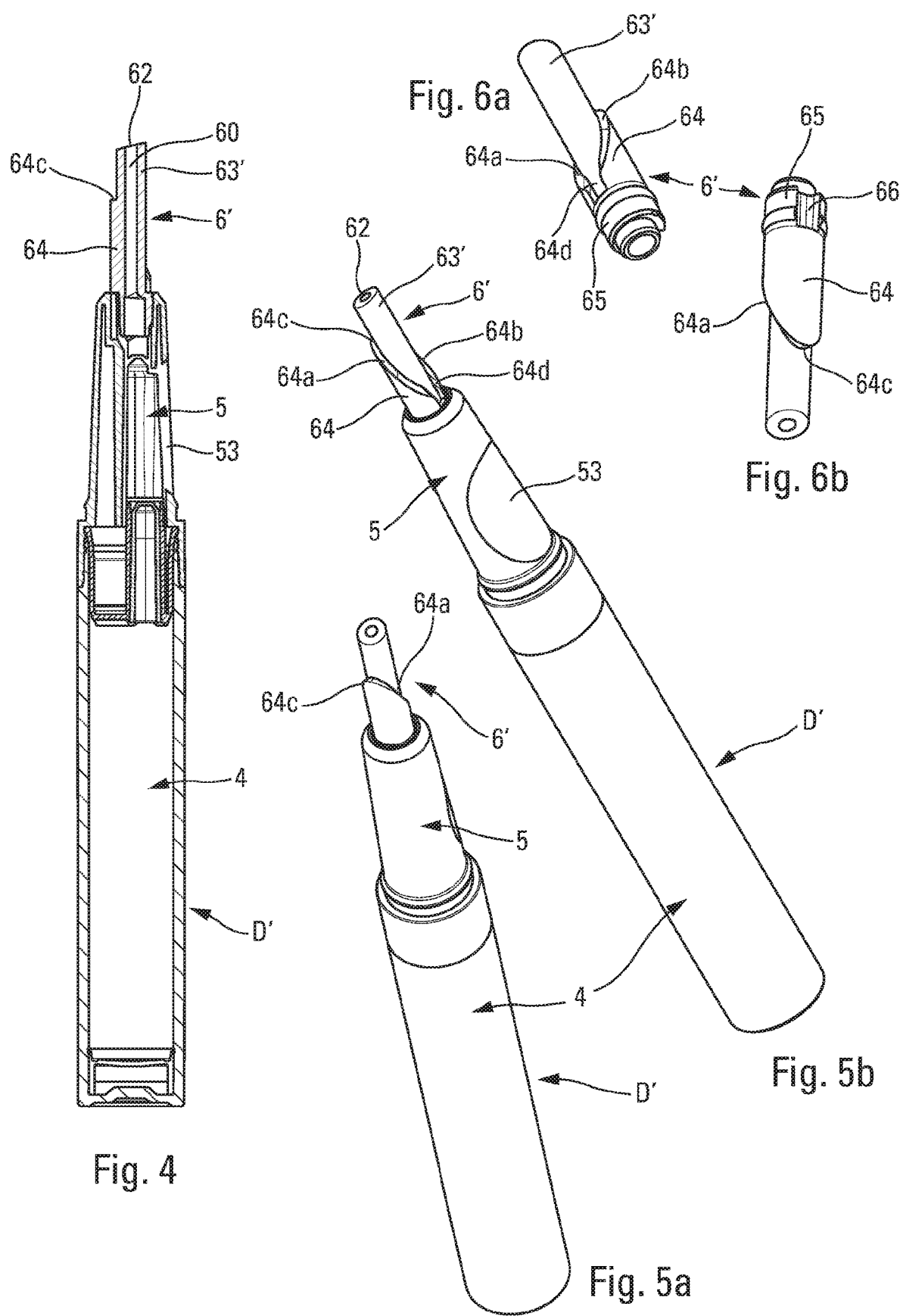

FLUID PRODUCT DISPENSING AND APPLICATION ASSEMBLY

CROSS REFERENCE TO RELATED APPLICATIONS

This application is a National Stage of International Application No. PCT/FR2018/050510, filed on Mar. 6, 2018, which claims priority from French Patent Application No. 1751930, filed on Mar. 9, 2017.

The present invention relates to a fluid dispenser and applicator assembly comprising: a hollow reception body; a fluid applicator surface that is mounted at a top end of the reception body and that is for coming into contact with a target, such as the skin; and a fluid dispenser comprising a reservoir, a pump, and a dispenser endpiece that defines an outlet surface in which a fluid dispenser orifice opens out. The assembly advantageously includes an activation module that emits waves, light, and/or electricity, and transmits them (it) to the applicator surface. Thus, the assembly makes it possible to apply a fluid to a target such as the skin, and to subject the skin to activation through the applicator surface either simultaneously, subsequently, or previously. Naturally, an advantageous field of application for the present invention is the field of cosmetics, but it may also be the field of pharmacy.

In the prior art, document WO 2015/170048 is already known, which describes a dispenser and applicator assembly of this type. It comprises a hollow reception body and a fluid applicator surface that is situated at a top end of the reception body and that includes a housing. The applicator surface is intended to come into contact with a target, such as the skin, and the fluid applicator surface includes a housing. The dispenser and applicator assembly also comprises a fluid dispenser having a reservoir, a pump, and a dispenser endpiece that defines a fluid dispenser orifice. The dispenser is received in removable manner in the reception body, with an insertion appendage of its dispenser endpiece being inserted in removable manner in the housing, so that the dispenser orifice opens out directly in the applicator surface. The dispenser is removable from the reception body through an open bottom end of the reception body that is remote from the top end. In addition, angular orientation means are provided so as to bring the fluid dispenser into a determined angular position relative to the reception body. More precisely, the dispenser endpiece and the housing present a corresponding cross-section imposing mutual engagement with a single angular orientation. Thus, in order to cause the dispenser endpiece to penetrate into its housing, it is necessary for the user to turn the dispenser in the reception body until the endpiece is in alignment with the housing. This is made all the more difficult as the dispenser is already received almost entirely in the reception body.

Document US2011/0190672 is also known, which describes a vibrator applicator comprising a casing containing a reservoir that is provided with a dispenser endpiece. A collar arranged on the casing contains a vibrator element that surrounds the dispenser endpiece. A thermal storage head is coupled to the vibrator element so as to cause it to vibrate: the head is movable relative to the casing. The head defines an applicator surface in which the dispenser endpiece opens out. The collar includes a lateral pusher for activating the vibrator element. The fluid is dispensed by squeezing the reservoir: a variant with a pump is described without going into detail. The dispenser is not intended to be disassembled and thus constitutes a unitary assembly.

More particularly, an object of the present invention is to improve the fluid dispenser and applicator assembly of document WO 2015/170048 by making it easier to insert the dispenser in a particular orientation in the reception body. In other words, an object of the invention is to improve the angular orientation means.

To do this, the present invention proposes that the angular orientation means cause the dispenser to turn as it is pushed into the reception body, until it reaches its determined angular position. Thus, the user no longer needs to turn the dispenser in the reception body and to locate by trial and error the precise angular orientation that makes it possible to engage the dispenser endpiece fully into its housing. Appropriate orientation of the dispenser in the reception body is now performed automatically: it suffices for the user to push the dispenser axially into the reception body. At best the axial thrust does not require any turning component, and at worst the user assists the dispenser with the turning movement caused by the angular orientation means. It should be observed that the final angular orientation is achieved, whatever the initial angular orientation.

In an advantageous embodiment, the angular orientation means include at least one helical cam-ramp. The cam may be formed by the dispenser or by the reception body. Advantageously, the angular orientation means include a lug that slides along the helical cam-ramp causing the dispenser to turn. The term "lug" should be understood to mean any member, part or profile that is capable of moving in sliding contact along the ramp or cam. Preferably, the angular orientation means include two helical cam-ramps that are joined together at a tip and that both lead to the determined angular position. Thus, the dispenser turns in the clockwise or anticlockwise direction depending on which ramp the lug is engaged. Whatever happens, the lug reaches the same position. The tip, formed at the tops of both ramps, makes it possible to avoid the lug blocking.

In a preferred practical embodiment, upstream from the insertion appendage, the dispenser endpiece forms two helical cam-ramps that are joined together at a tip and that both lead to an abutment notch, the reception body forming a stationary lug that slides along one of the two helical cam-ramps until it becomes housed in the abutment notch.

In another aspect of the invention, the dispenser and applicator assembly may include a removable bottom wall that co-operates with the reception body so as to close the bottom end, the removable bottom wall acting to push the dispenser towards the top end, pressing the stationary lug into the abutment notch. The bottom wall may even be used to move the dispenser axially into the reception body and to cause it to turn.

According to another advantageous characteristic, the dispenser defines a longitudinal axis X that passes via the reservoir, the pump, and the dispenser endpiece, the pump including a lateral actuator that is movable transversally relative to the longitudinal axis X, the reception body including a lateral pusher that is arranged facing the lateral actuator so as to make it possible to move the lateral actuator by pressing laterally on the lateral pusher. By means of the angular orientation means of the invention, the lateral actuator is guaranteed always to be positioned at the lateral pusher. The user no longer even needs to give this any thought, given that the dispenser is now oriented correctly in the reception body in automatic manner.

The angular orientation means of the invention generates yet another advantage, namely that the insertion appendage may present a cross-section that is substantially or completely circular. This does not apply in document WO 2015/170048 in which the dispenser endpiece and the housing present a corresponding cross-section imposing mutual engagement with a single angular orientation. In the invention, the corresponding cross-section of the dispenser endpiece and the housing may be of any shape.

In another advantageous aspect of the invention, the dispenser endpiece defines an outlet surface that presents an outline having a shape that corresponds to the shape of the housing at least at the applicator surface, such that the dispenser endpiece closes the housing in sealed manner, at least at the applicator surface. Thus, there can be fluid only at the applicator surface.

In an advantageous embodiment of the invention, the reception body houses an activation module that is suitable for producing electromagnetic waves such as light, vibration, and/or electricity such as iontophoresis, at the applicator surface.

The spirit of the invention resides in the dispenser being angularly oriented in the reception body automatically, indeed even imperceptibly, with the dispenser being inserted axially into the reception body, with this being done by the angular orientation means of the invention and starting from any angular position. This makes it possible to orientate correctly the dispenser endpiece in its housing and/or the lateral actuator facing the lateral pusher. The angular orientation means make it possible to transform an axial component into a radial or turning component: a preferred technique uses a helical ramp or cam over which there slides any element or profile.

The invention is described below in greater detail with reference to the accompanying drawings, which show an embodiment of the invention by way of non-limiting example.

In the figures:

FIG. 1 is a vertical-section view through a fluid dispenser and applicator assembly of the prior art;

FIG. 2 is a greatly enlarged view of the top portion of FIG. 1;

FIG. 3 is a horizontal cross-section view on section line A-A in FIG. 2;

FIG. 4 is a vertical section view through a fluid dispenser of the invention;

FIGS. 5a and 5b are perspective views from different angles of the FIG. 4 fluid dispenser;

Figure 7A:
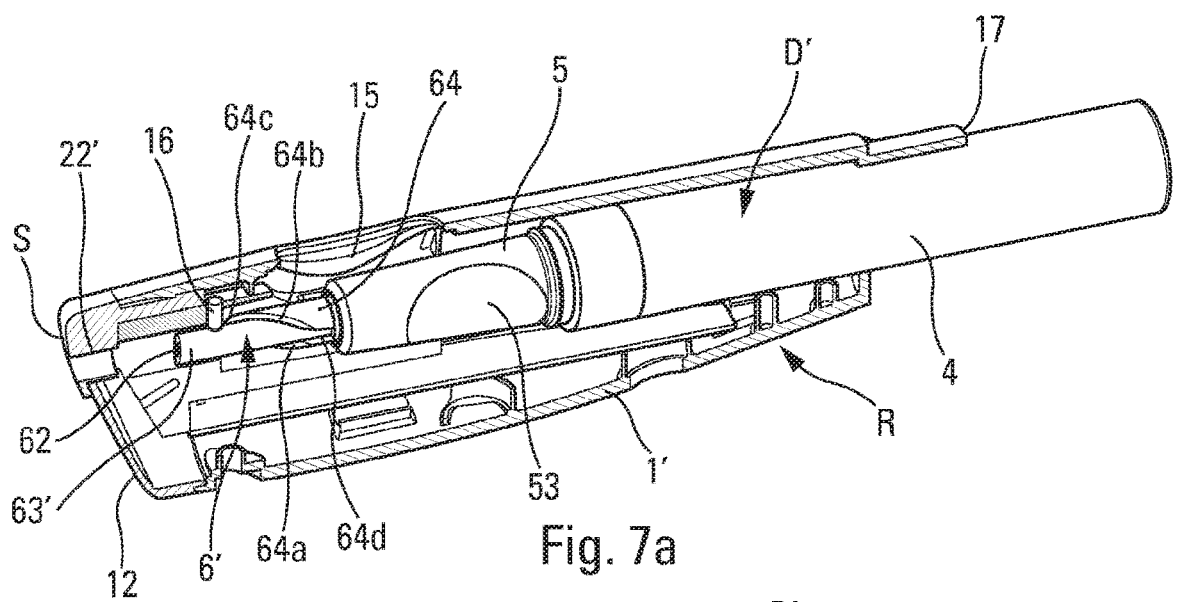
Figure 7B:
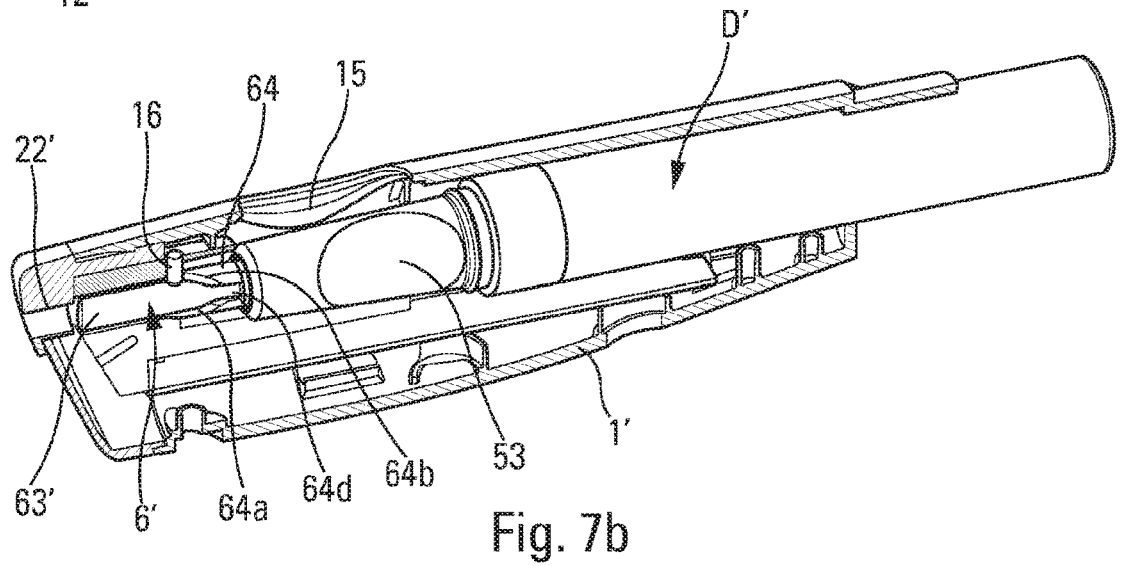
Figure 7C:
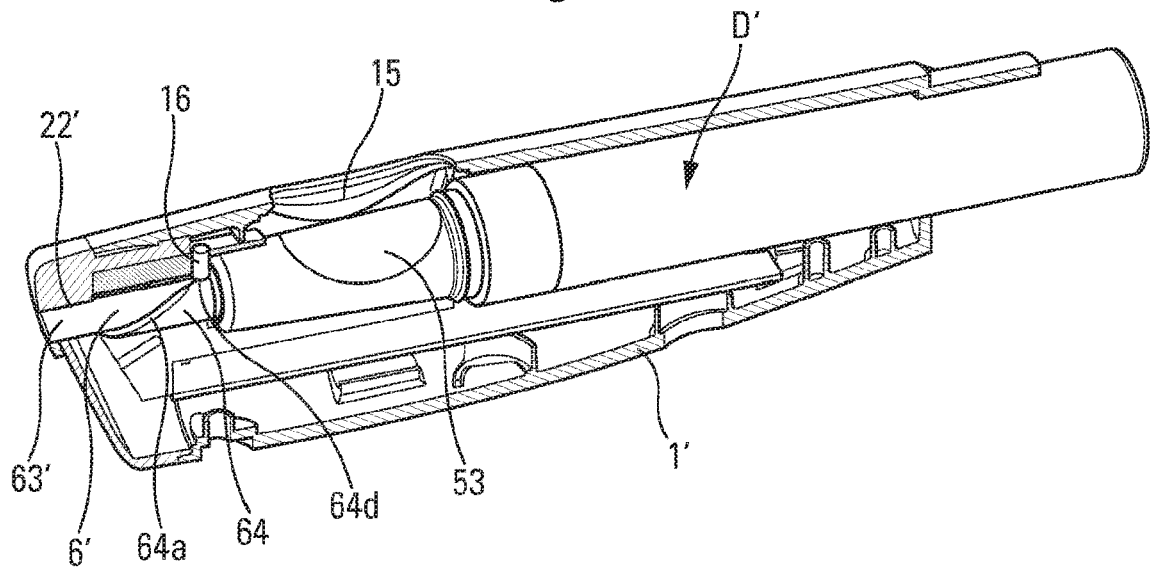

FIGS. 6a and 6b are perspective views from different angles of the dispenser endpiece of the fluid dispenser in FIGS. 4, 5a, and 5b; and FIGS. 7a, 7b, and 7c are perspective views, cut away in part, of a fluid dispenser and applicator assembly of the invention, using the fluid dispenser in FIGS. 4, 5a, and 5b, for the purpose of showing various steps while inserting the dispenser.

As mentioned above, FIGS. 1 to 3 show a fluid dispenser and applicator assembly of the prior art, and specifically the fluid dispenser and applicator assembly of document WO 2015/170048. The general structure and even most of the details of the dispenser and applicator assembly of the prior art may be reproduced approximately, or exactly, in the context of the present invention, except for the orientation or indexer means of the dispenser in the reception body.

The dispenser and applicator assembly of the prior art presents an elongate or slender shape that may be similar to the shape of a pen. It should also be observed that its cross-section is not constant, since it varies significantly from bottom to top. Specifically, in the proximity of its bottom end, the dispenser and applicator assembly presents a cross-section that is generally round or circular, while at the section line A-A, which is generally situated in the proximity of the top end, the dispenser and applicator assembly presents a cross-section that is egg shaped (FIG. 3). The top face of the assembly forms an applicator surface S that inclines or slopes towards one side.

With reference to FIG. 1, it is possible to see the various component elements of the dispenser and applicator assembly of the invention. Initially, it should be observed that it comprises three main distinct units, namely a fluid dispenser D, a reception unit R, and an applicator unit A. The dispenser D is received in removable manner inside the reception unit R that comprises a reception body 1 having an inside that is hollow. The applicator unit A is mounted on and in the body 1, advantageously in removable manner. Thus, the two units D and A are preferably received in removable manner on and in the body 1 from the two opposite ends 17 and 12 respectively. This is the general structure of the dispenser and applicator assembly of the prior art, which may be reproduced in the context of the invention.

In greater detail, the body 1 of the reception unit R is open at its top and bottom ends 12, 17 so as to be able to receive the units A and D. The bottom end 17 is advantageously threaded so as to receive a removable end wall 7 by screw-fastening. It should be observed that the removable end wall 7 is provided with a piece of elastic material 74 that may be foam or an elastomer. The inside of the removable end wall 7 forms a space that communicates upwardly with the inside of the body 1, which itself defines a reception space 1a. Beyond the reception space 1a, the inside of the body 1 is divided into two compartments 1b and 1c by a separating partition 13. The compartment 1b extends axially running on from the space 1a, while the compartment 1c extends laterally, where the body 1 defines its egg shape. The bottom end of the partition 13 forms a snap-fastener edge 14, as described below. Level with the compartment 1b, the body 1 is provided with a lateral pusher 15 that is movable transversally relative to the longitudinal axis of the reception body 1. The pusher 15 may be moved purely in translation or it may be deformed elastically. By way of example, it is possible to envisage molding the pusher 15 onto the reception body 1, using an elastomeric material. In a variant, it is also possible to envisage a pusher 15 that moves completely independently of the body 1. It is also possible to envisage not having a pusher 15 but only a window. It should also be observed that the separator partition 13 extends into the proximity of the top end 12. The reception body 1 may be made merely by injection molding plastics material, or it may even be made of metal.

In this embodiment, the applicator unit A results from combining an applicator head 2 and an activation module 3. As can be seen in FIGS. 1 and 2, the applicator head 2 includes an axial housing 22 that is formed by a cylindrical tube having a cross-section that presents a geometrical shape that is complex, e.g. the shape of a crescent. The housing 22 is upwardly connected to an applicator-surface area 21 that, in this embodiment, is formed with two openings, namely a first opening corresponding to the mouth of the housing 22, and a second opening for the activation module 3. More precisely, the activation module 3 includes an applicator-surface section 31 that closes the corresponding opening of the head 2 in such a manner as to complete the applicator-surface area 21 of the head 2 in continuous and smooth manner. In other words, the activation module 3 fits in the opening of the applicator head, so that the applicator-surface section 31 of the activation module 3 finishes off the applicator-surface area of the head 2 without creating any projecting or recessed discontinuities. Consequently, assembling the module 3 and the head 2 together makes it possible to create an applicator surface S having a single opening that, at this stage, is formed by the mouth of the housing 22. In FIGS. 1 and 2, it should be observed that the applicator-surface section 31 occupies the portion of the applicator surface S that slopes the most. The applicator head 2 also includes a peripheral skirt 23 that fits in the top end 12 of the hollow body 1. In addition, the wave-generator module 3 extends inside the reception space 1c, and advantageously presents a snap-fastener profile 34 that is suitable for co-operating with the bottom edge 14 of the separator partition 13. In this way, the applicator unit A may be mounted in completely stable manner on and in the hollow body 1.

In the invention, the activation module 3 makes it possible to generate any type of electromagnetic, vibratory, electrical, etc. wave or radiation, e.g. visible, infrared, or ultraviolet light, or microwaves, etc., or even ultrasound, or mechanical vibration. The module 3 may also generate heat or cold (thermal waves) so as to impart a hot or cold effect on contact with the skin. Iontophoresis is also a technology that may be incorporated in the activation module 3.

The fluid dispenser D comprises a fluid reservoir 4, a pump 5, and a dispenser endpiece 6, as can be seen in FIGS. 1 and 2.

By way of example, the reservoir 4 may be in the form of a slide cylinder in which there is received a follower piston that is adapted to slide in the cylinder as the fluid is extracted from the reservoir. The top of the cylinder forms a neck 45. Instead of this particular reservoir, it is also possible to envisage a simpler reservoir in which the working volume does not vary, or a reservoir with a flexible pouch.

The pump 5 includes a fastener ring 54 that enables it to be mounted on the neck 45 of the reservoir 4. The pump 5 includes a pump chamber 50 that, at its bottom end, is provided with an inlet valve 51, e.g. in the form of a slotted shutter. At its top end, the pump chamber 50 includes an outlet valve 52 that may also be made in the form of a slotted shutter, for example. Furthermore, the pump chamber 50 includes a lateral actuator 53 that makes it possible to reduce the working volume of the pump chamber 50, and thus force the fluid through the outlet valve 52. The lateral actuator 53 is movable perpendicularly to the longitudinal axis X of the dispenser D. The movement may be in translation or by elastic deformation. In the embodiment used to illustrate the present invention, the actuator 53 is in the form of a flexible wall of the pump chamber 50 that is made by a method of bi-injection or of overmolding, for example. The pump 5 may thus be referred to as a flexible-diaphragm pump, in the sense that a movable wall of the chamber is actuated directly in order to put the fluid under pressure. At its top end, the pump 5 forms a mounting well 55 for mounting the dispenser endpiece 6. The mounting well 55 is advantageously provided with keying means 56, e.g. in the form of a projecting profile or a recess, making it possible to impose the angular orientation of the endpiece 6 in the well 55.

The dispenser endpiece 6 thus includes a mounting stub 65 that is engaged, and advantageously snap-fastened, inside the mounting well 55. The mounting stub 65 includes a keying profile 66 that fits perfectly in the keying means 56 of the well 55, so as to impose the angular orientation of the dispenser endpiece 6 on the pump 5. In this way, the endpiece is always oriented in the same way relative to the lateral actuator 53 that extends on one side only of the pump 5. Above the mounting stub 65, the dispenser endpiece 6 forms an insertion appendage 63 having a cross-section that presents a shape that corresponds to the shape of the housing 22 formed by the applicator head 2. It is similar to the shape of a crescent. The side wall of the insertion appendage 63 may be a non-circular cylinder over its entire height. At its top end, the appendage 63 forms a substantially-plane outlet surface 61 that is perforated with a dispenser orifice 62, forming the outlet of an outlet duct 60 that passes through the appendage 63 and the mounting stub 65, as can be seen clearly in FIG. 2.

Once the dispenser endpiece 6 is mounted on the pump 5, as can be seen in FIG. 2, it can be seen that the outlet valve 51 communicates directly with the outlet duct 60. Thus, by depressing the lateral actuator 53, the working volume of the pump chamber 50 is reduced, and fluid under pressure is forced through the outlet valve 52, from where it can flow through the outlet duct 60 until it reaches the dispenser orifice 62 situated at the outlet surface 61. When the pressure on the lateral actuator 53 is relaxed, the outlet valve 52 closes and the inlet valve 51 opens under the effect of the suction created in the pump chamber 50, thus enabling fluid to be sucked up from the reservoir 4, in which the follower piston 42 then moves towards the pump 5.

As can be understood from FIG. 1, the dispenser D is inserted inside the hollow body 1 through its bottom end 17, after removing the removable end wall 7. The dispenser D is thus inserted axially through the space 1a, then through the space 1b until the dispenser endpiece 6 penetrates into the housing 22 of the applicator head 2. As explained above, it is necessary to orientate the dispenser D angularly, so that its insertion appendage 63 is engaged inside the housing 22. The angular orientation is a single angular orientation. It should thus be observed that the co-operation between the insertion appendage 63 and the housing 22 forms angular orientation or indexer means, making it possible to orientate the dispenser D angularly in the hollow reception body 1, in particular so that the lateral actuator 53 is arranged facing the pusher 15 (or the window that could replace it). The angular orientation or indexer means require the user to locate the correct position by trial and error, by turning the dispenser D in the hollow body 1 until the user feels or perceives that the insertion appendage 63 is engaged in the housing 22.

It is thus possible to engage the appendage 63 fully inside the housing 22 until the outlet surface 61 comes level with the applicator surface S so as to finish it off. This can be seen in FIG. 2. It can be seen that the outlet surface 61 becomes completely flush with the applicator-surface area 21 of the head 2 so as to finish it off. Finally, only the dispenser orifice 62 breaks the continuity of the applicator surface S. In order to guarantee that the appendage 63 is engaged fully in the housing 22, use is made of the removable end wall 7 having flexible material 64 that comes into contact with the end wall of the reservoir 4 so as to push it upwards, and establish sealing at the housing 22. In this respect, it should also be observed that the bottom end of the reservoir 4 projects out from the hollow body 1 when the removable end wall 7 is removed, so as to make it easy to grip the dispenser by its reservoir 4 in order to remove it from the hollow body 1. As a result, the dispenser D is received in removable manner inside the hollow body 1 and the head 2. It should also be observed that the imposed angular orientation of the appendage 63 inside the housing 22 makes it possible to arrange the lateral actuator 53 facing the pusher 15 of the hollow body 1.

With such a design, the dispenser D is received in removable manner inside the reception unit R and inside the housing 22 of the applicator unit A. In this way, the dispenser D and the applicator unit A may be replaced at will as a function of requirements. By way of example, it is possible to envisage that a particular dispenser dispensing a particular fluid is associated with a particular applicator unit.

It should also be observed that the fluid dispensed by the dispenser D leaves the dispenser only at the applicator surface S, such that no fluid can remain inside the reception unit R once the dispenser has been removed. Furthermore, as a result of the applicator surface S being completely smooth and continuous, it can easily be cleaned by rubbing or wiping. Thus, when a user wishes to change a dispenser, it suffices for the user to clean the applicator surface S beforehand, then to remove the dispenser and replace it with another. No soiling or fluid deposit can be observed.

Although the fluid dispenser and applicator assembly described above with reference to FIGS. 1 to 3 shows the prior art, all of its characteristics and the way it is arranged, except for the orientation means 22, 63, may be reproduced, in identical or modified form, in the context of the present invention.

Reference is made below to FIGS. 4, 5a, 5b, 6a, and 6b in order to describe a dispenser D' of the invention, which dispenser differs from the dispenser D only in the dispenser endpiece: the reservoir 4 and the pump 5 may be entirely identical to the reservoir and pump in FIGS. 1 to 3. In contrast, the dispenser endpiece 6' is different. Specifically, in addition to the anchor stub 65 (which may be identical to the mounting stub of the endpiece 6) and the insertion appendage 63' (that differs from the insertion appendage of the endpiece 6) the endpiece 6' includes an orientation profile 64 that is situated between the anchor stub 65 and the insertion appendage 63'. In this particular embodiment, the orientation profile 64 comprises two helical cam-ramps 64a and 64b that extend in sloping manner around an extension towards the bottom of the insertion appendage 63'. The two helical cam-ramps 64a and 64b are joined together at the top, forming a kind of tip 64c. Although the tip 64c is more or less rounded in the figures, it may also be angular or sharp. Both of the helical cam-ramps 64a and 64b also lead to an abutment notch 64d that is situated just above the anchor stub 65. The tip 64c and the abutment notch 64d are thus situated in diametrically-opposite manner, but offset axially, since the tip 64c is adjacent or close to the insertion appendage 63' and the abutment notch 64d is adjacent or close to the anchor stub 65. The abutment notch 64d is oriented so as to be in alignment with the lateral actuator 53. The two helical cam-ramps 64a and 64b thus form a kind of sloping projecting collar that surrounds the base of the insertion appendage 63'.

It should be observed that the insertion appendage 63', and its base situated at the two helical cam-ramps, presents a cross-section that is round or circular, unlike the cross-section of the insertion appendage 63 in FIGS. 1 to 3. The orientation of the dispenser is thus no longer determined by the insertion appendage, but by the two helical cam-ramps, the tip 64c, and the abutment notch 64d.

With reference to FIGS. 7a, 7b, and 7c, it is possible to see how the dispenser D' co-operates with the hollow body 1' of the reception unit R. The figures show the fluid dispenser and applicator assembly of the invention with the dispenser D' in perspective, the hollow body in cross-section and the applicator unit A removed. It should be observed that the hollow body 1' includes a lug 16 that is situated between the housing 22' and the pusher 15. The lug 16 projects radially inwards so as to come in the proximity of, or in contact with, the insertion appendage 63', as can be seen in FIG. 7a. In order to reach the insertion position, the user merely has to insert the dispenser D' into the hollow body 1' through its open bottom end (after removing the bottom wall 7). The dispenser D' is engaged axially in the hollow body 1' without any turning component, until the lug 16 comes into contact with the orientation profile 64. Depending on the random orientation of the dispenser D' in the hollow body 1', the lug comes into contact either with the tip 64c, or with one of the helical cam-ramps 64a or 64b, or best of all, the lug 16 may become housed directly in the abutment notch 64d, so the orientation profile 64 then serves no purpose at all. However, the lug 16 usually comes into contact with one of the helical cam-ramps 64a or 64b, and thus causes the dispenser D' to turn about its own axis. The lug slides along the ramp 64a or 64b until it arrives in register with the abutment notch 64d. The dispenser D' may then continue its axial movement (without any turning component) until the lug comes into abutment with the bottom of the abutment notch 64d (FIG. 7c). Simultaneously, the insertion appendage 63' is engaged in its housing 22'. The insertion appendage 63' may even be engaged in its housing 22' while the lug 16 is still sliding over one of the ramps, given that the cross-sections of the insertion appendage 63' and of its housing 22' are round or circular.

In FIG. 7a, the lug 16 practically comes into contact with the tip 64c, but beside the ramp 64b. It then slides over the ramp 64b, as shown in FIG. 7b. Finally, it becomes housed in the notch 64d, as can be seen in FIG. 7c. The lateral actuator 53 is thus positioned facing the pusher 15, and the insertion appendage 63' is engaged fully in its housing 22'. The end wall 7 may thus be put back into place.

The figures show a particular embodiment in which the orientation profile is formed on the dispenser endpiece and the lug is formed on the hollow body. Without going beyond the ambit of the invention, it is also possible to envisage the following alternative embodiments:

The orientation profile is formed by the hollow body (or it is secured to the hollow body), and the lug is formed by the dispenser.

The orientation profile includes only one cam-ramp that forms a tip and leads to the abutment notch. The single ramp thus extends over nearly 360°.

The cam-ramp is formed on the housing 22.

Whatever the embodiment, the orientation profile co-operates with the lug (or its equivalent) to form angular orientation or indexer means, making it possible to orientate the dispenser D' angularly in the hollow reception body 1', in particular so that the lateral actuator 53 is arranged facing the pusher 15 (or the window that could replace it), and this without the user needing to locate any particular angular position. Specifically, whatever the angular orientation of the dispenser D' while being engaged in the hollow body, it is automatically orientated in appropriate manner, without the user even noticing it or even realizing it. The dispenser D' may be oriented, at least in part, while putting the end wall 7 in place.

By means of the invention, the angular orientation means cause the dispenser to turn as it is pushed into the reception body, until it reaches its determined angular position.

The invention claimed is:

1. A fluid dispenser and applicator assembly comprising:
a hollow reception body, a fluid applicator surface being situated at a top end of the reception body and being intended to come into contact with a target, such as the skin, the fluid applicator surface including a housing; and
a fluid dispenser comprising a reservoir, a pump, and a dispenser endpiece that defines a fluid dispenser orifice, the dispenser being received in removable manner in the reception body, with an insertion appendage of its dispenser endpiece being inserted in removable manner in the housing, so that the dispenser orifice opens out directly in the applicator surface, the dispenser being removable from the reception body through an open bottom end of the reception body that is remote from the top end, angular orientation means being provided so as to bring the fluid dispenser into a determined angular position relative to the reception body;

wherein the angular orientation means cause the dispenser to turn as it is pushed into the reception body, until it reaches its determined angular position; and wherein the angular orientation means include two helical cam-ramps that are joined together at a tip and that both lead to the determined angular position.

2. A fluid dispenser and applicator assembly comprising:

a hollow reception body, a fluid applicator surface being situated at a top end of the reception body and being intended to come into contact with a target, such as the skin, the fluid applicator surface including a housing; and a fluid dispenser comprising a reservoir, a pump, and a dispenser endpiece that defines a fluid dispenser orifice, the dispenser being received in removable manner in the reception body, with an insertion appendage of its dispenser endpiece being inserted in removable manner in the housing, so that the dispenser orifice opens out directly in the applicator surface, the dispenser being removable from the reception body through an open bottom end of the reception body that is remote from the top end, angular orientation means being provided so as to bring the fluid dispenser into a determined angular position relative to the reception body;

wherein the angular orientation means cause the dispenser to turn as it is pushed into the reception body, until it reaches its determined angular position; and wherein, upstream from the insertion appendage, the dispenser endpiece forms two helical cam-ramps that are joined together at a tip and that both lead to an abutment notch, the reception body forming a stationary lug that slides along one of the two helical cam-ramps until it becomes housed in the abutment notch.

3. An assembly according to claim 2, including a removable bottom wall that co-operates with the reception body so as to close the bottom end, the removable bottom wall acting to push the dispenser towards the top end, pressing the stationary lug into the abutment notch.

4. An assembly according to claim 1, wherein the dispenser defines a longitudinal axis X that passes via the reservoir, the pump, and the dispenser endpiece, the pump including a lateral actuator that is movable transversally relative to the longitudinal axis X, the reception body including a lateral pusher that is arranged facing the lateral actuator so as to make it possible to move the lateral actuator by pressing laterally on the lateral pusher.

5. An assembly according to claim 1, wherein the insertion appendage presents a cross-section that is substantially circular.

6. An assembly according to claim 1, wherein the dispenser endpiece defines an outlet surface that presents an outline having a shape that corresponds to the shape of the housing at least at the applicator surface, such that the dispenser endpiece closes the housing in sealed manner, at least at the applicator surface.

7. An assembly according to claim 1, wherein the reception body houses an activation module that is suitable for producing electromagnetic waves such as light, vibration, and/or electricity such as iontophoresis, at the applicator surface.

8. An assembly according to claim 1, including a removable bottom wall that co-operates with the reception body so as to close the bottom end, the removable bottom wall acting to push the dispenser towards the top end, pressing the stationary lug into the abutment notch.

9. An assembly according to claim 2, wherein the dispenser defines a longitudinal axis X that passes via the reservoir, the pump, and the dispenser endpiece, the pump including a lateral actuator that is movable transversally relative to the longitudinal axis X, the reception body including a lateral pusher that is arranged facing the lateral actuator so as to make it possible to move the lateral actuator by pressing laterally on the lateral pusher.

10. An assembly according to claim 2, wherein the insertion appendage presents a cross-section that is substantially circular.

11. An assembly according to claim 2, wherein the dispenser endpiece defines an outlet surface that presents an outline having a shape that corresponds to the shape of the housing at least at the applicator surface, such that the dispenser endpiece closes the housing in sealed manner, at least at the applicator surface.

12. An assembly according to claim 2, wherein the reception body houses an activation module that is suitable for producing electromagnetic waves such as light, vibration, and/or electricity such as iontophoresis, at the applicator surface.

\* \* \* \* \*